(12) United States Patent
O'Lenick, Jr. et al.

(10) Patent No.: US 6,869,977 B1
(45) Date of Patent: Mar. 22, 2005

(54) SKIN MOISTURIZATION COMPOUND

(75) Inventors: Anthony J. O'Lenick, Jr., Dacula, GA (US); Dean A. Smith, Chattanooga, TN (US)

(73) Assignee: Colonial Chemical Inc., South Pittsburg, TN (US)

( * ) Notice: Subject to any disclaimer, the term of this patent is extended or adjusted under 35 U.S.C. 154(b) by 0 days.

(21) Appl. No.: 10/820,935

(22) Filed: Apr. 9, 2004

(51) Int. Cl.[7] ............................................. A01N 33/12
(52) U.S. Cl. ...................... 514/847; 514/642; 564/292; 424/401
(58) Field of Search ................................ 514/847, 642; 564/292; 424/401; 510/133, 119, 120, 130, 132, 135, 136, 141; 568/704, 713

(56) References Cited

U.S. PATENT DOCUMENTS 5,922,331 A * 7/1999 Mausner .................... 424/401
6,265,364 B1 * 7/2001 Kilpatrick-Liverman et al. ......................... 510/133
6,414,170 B1 * 7/2002 Kim et al. .................... 554/52

OTHER PUBLICATIONS

Buriks et al., J. Org. Chem., vol. 52, No. 23, 1987, pp. 5247–5254.*

* cited by examiner

Primary Examiner—Johann Richter
Assistant Examiner—Chukwuma Nwaonicha

(57) ABSTRACT

The present invention discloses a series of quaternary nitrogen compounds in which the four groups surrounding nitrogen are (a) one glyceryl portion, (b) two methyl groups and (c) a hydroxy ethyl group. The compound of the present invention is an outstanding moisturizer when applied to skin.

3 Claims, No Drawings

SKIN MOISTURIZATION COMPOUND

BACKGROUND OF THE INVENTION

Skin moisturization has been a desired skin benefit for many years. Dry skin can be a result of environmental effects such as sunlight, dry winter air, dermatological condition as well as the application of cleansing materials to the skin such as soap or other harsh detergents which remove oils that are naturally present on the surface of the skin thereby resulting in a loss of moisturization.

U.S. Pat. No. 6,265,364 issued to Kilpatrick-Liverman, et al in Jul. 24, 2001 discloses a composition useful for moisturizing skin.This patent is incorporated herein by reference.

U.S. Pat. No. 6,475,965 also issued Nov. 5, 2002 to Kilpatrick-Liverman, et al describes a skin moisturizing composition comprising a choline salt. This patent is a continuation-in-part of application U.S. Pat. No. 6,265,364. This patent is incorporated herein by reference.

The Kilpatrick-Liverman, et al patents, disclose that choline salt and related compounds are powerful moisturizing agents for skin. Even in a rinse off cleansing composition such material(s) or mixture thereof brings about substantially more moisture on the skin. This can be a statistically significant measurable quantity of moisture on the skin.

The present invention discloses a series of new compounds that are surprisingly more effective than the compounds disclosed in U.S. Pat. No. 6,475,965.

THE INVENTION

Objective of the Invention

It is the objective of the present invention to provide a new cationic material which provides outstanding moisturization to the skin and a process foe moisturizing skin which comprises contacting the skin with the novel moisturization agent. Other objectives will become clear in reading the disclosure.

SUMMARY OF THE INVENTION

The present invention is directed to a series of new cationic materials and a process for their use as moisturizing agents on skin. The compounds of the present invention conform to the following structure:

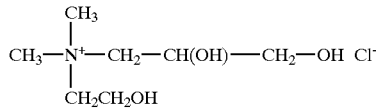

The compounds of the present invention can be used to moisturize the skin. Significant measurable increases in moisture can be obtained when the composition is applied to the skin. The composition can be in the form of a liquid, solid, or gelled cleansing formulation.

The second aspect of the present invention is a process for moisturizing the skin which comprises contacting the skin with an effective moisturizing concentration of a compound conforming to the following structure;

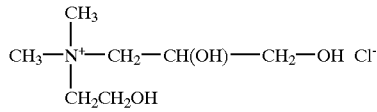

The effective moisturizing concentration of the compound ranges from 0.05% to about 15% by weight, with a preferred concentration ranging from 0.1% to 10 wt % by weight.

DETAILED DESCRIPTION OF THE INVENTION

The moisturizing compound of the present invention is made via the following reaction;

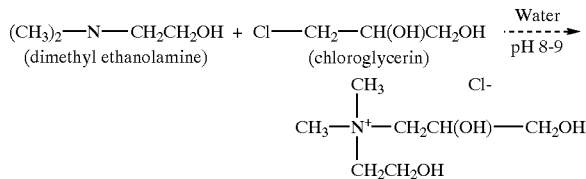

The product has a glyceryl moiety, as well as a 2-hyodoxyethyl moiety, making the product a better moisturizer.

The moisturizing compound can be formulated into a variety of compositions, liquid, solid and gel-like for delivery of its improved moisturizing benefit. When formulated with a solid, the moisturizing compound can be present with large or small quantities of soap with the remainder of the surfactant being none, smaller or larger quantities of anionic surfactant such as synthetic surfactant. When formulated with a liquid or gel composition, the moisturizing compound is formulated with various amounts of water depending upon the usage of the composition as a cleansing composition, as well as various surfactants of an anionic, nonionic, cationic, amphoteric type, or mixtures thereof. The liquid or gel formulations, particularly the liquids can be formed as a cream or lotion or free flowing liquid which has cleaning abilities, moisturizing and/or conditioning abilities, or a mixture of the cleansing with the moisturizing and/or conditioning benefits. By conditioning is meant increasing the smoothness or suppleness of the skin. By moisturizing is meant the actual increasing of water content of the skin.

Other additional conditioning and moisturizing agents also can be present in the when compounding compositions containing the compounds of the present invention. Typical moisturizing or conditioning materials include urea, lactic acid, pyrrolidone carboxylic acid, amino acids and salts of the acids mentioned.

Preferred Embodiment

In a preferred embodiment the effective moisturizing concentration of the compound ranges from 0.05% to about 15% by weight;

In another preferred embodiment the effective moisturizing concentration of the compound ranges from 0.1% to 10 wt % by weight.

EXAMPLES

Raw Materials

Example 1

Dimethyl-Ethanolamine

Dimethyl ethanolamine is an article of commerce, commercially available from a variety of sources. It conforms to the following structure.

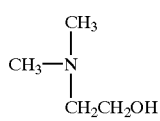

Example 2

Chloroglycerin

Chloroglycerin is an article of commerce available from a variety of sources including Phoenix Chemical Somerville N.J. It conforms to the following structure;

Compound of the Present Invention

Chloroglycerin is reacted with dimethylethanolamine under aqueous conditions to give the product of the present invention.

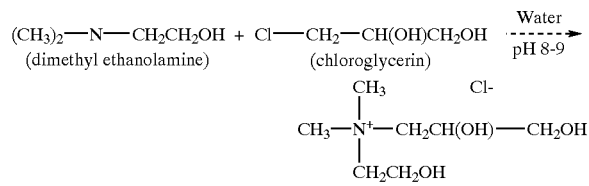

Example 3

Product-35% Active

To 650.0 grams of water is added 147.0 grams of dimethyl ethanolamine, and 203.0 grams of chloroglycerin. The reaction mass is heated to 80-90° C., and held for 4-8 hours. During that time the % inorganic chloride ion reaches 97% of theoretical. During the reaction time the pH is kept between 8-9. The solution is cooled and used without purification.

APPLICATIONS

The effect of moisturization can be measured by the appearance of the skin when treated. Untreated skin that is in need of moisturization is rough, scaly and dry looking under the dissection microscope. The application of the moisturization solution to the skin and its effect upon minimizing roughness, scaling and dry appearance is a good measure of moisturization. We performed such an evaluation and rated the performance of a scale of 1 to 5.1 being poor and 5 being best.

| Sample | Rating |
|---|---|
| Water | 1 |
| 5% Choline | 4 |
| 5% Glycerin | 2 |
| 5% Example 3 | 5 |

The compound of the present invention is a very effective moisturization agent when applied to rough dry skin.

While the illustrative embodiments of the invention have been described with particularly, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A process for moisturizing skin which comprises contacting the skin with an effective moisturizing concentration of a compound conforming to the following structure;

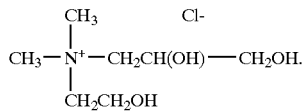

2. A process of claim 1 wherein said effective moisturizing concentration ranges from 0.05% to about 15% to weight.

3. A process of claim 1 wherein said effective moisturizing concentration ranges from 0.1% to 10 wt % by weight.

* * * * *